US009433397B2

(12) United States Patent
Anquez et al.

(10) Patent No.: US 9,433,397 B2
(45) Date of Patent: Sep. 6, 2016

(54) METHOD AND DEVICE FOR DETERMINING THE ELASTIC MODULUS OF A BIOLOGICAL TISSUE

(71) Applicant: Theraclion, Malakoff (FR)

(72) Inventors: Jérémy Anquez, Paris (FR); Francois Lacoste, Gentilly (FR); Sylvain Yon, Bagneux (FR)

(73) Assignee: THERACLION, Malakoff (FR)

( * ) Notice: Subject to any disclaimer, the term of this patent is extended or adjusted under 35 U.S.C. 154(b) by 571 days.

(21) Appl. No.: 13/687,574

(22) Filed: Nov. 28, 2012

(65) Prior Publication Data
US 2013/0144162 A1  Jun. 6, 2013

(30) Foreign Application Priority Data

Dec. 1, 2011 (EP) .................................... 11191556

(51) Int. Cl.
*A61B 8/00* (2006.01)
*A61B 8/08* (2006.01)
(52) U.S. Cl.
CPC .............. *A61B 8/485* (2013.01); *A61B 8/085* (2013.01)
(58) Field of Classification Search
CPC ...... A61B 5/048; A61B 5/415; A61B 5/418; A61B 8/08; A61B 8/485; A61B 5/031; A61B 8/04; A61B 8/488
USPC .............................. 600/407, 437, 441, 443
See application file for complete search history.

(56) References Cited

U.S. PATENT DOCUMENTS 6,014,473 A * 1/2000 Hossack et al. .............. 382/294
8,965,487 B2 * 2/2015 Bouma ......................... 600/476
2002/0095087 A1 * 7/2002 Mourad et al. ............... 600/442
2006/0079773 A1 * 4/2006 Mourad et al. ............... 600/438
2008/0249408 A1 * 10/2008 Palmeri et al. ............... 600/438
2008/0294049 A1   11/2008 Guracar
2010/0191113 A1   7/2010 Hazard et al.
2010/0317971 A1 * 12/2010 Fan et al. ...................... 600/439
2012/0065507 A1   3/2012 Brunke

FOREIGN PATENT DOCUMENTS

WO  2011/007278  1/2011
WO  2011/132014  10/2011

OTHER PUBLICATIONS

Palmeri et al., "Quantifying Hepatic Shear Modulus In Vivo Using Acoustic Radiation Force", Ultrasound in Med. & Biol., vol. 34, No. 4, pp. 546-558, 2008, USA.
Bercoff, "ShearWave Elastography", Supersonic Imagine The Theragnostic Company, White Paper, XP007920586, 2008, France.

* cited by examiner

*Primary Examiner* — Joel Lamprecht
(74) *Attorney, Agent, or Firm* — Davis & Bujold PLLC; Michael J. Bujold

(57) ABSTRACT

To determine the elastic modulus of biologic tissue, a sequence of elasticity images and a sequence of B-mode ultrasound images are acquired simultaneously. Then, at least one sub-sequence of the B-mode ultrasound images representing a resting state is generated from said sequence of B-mode ultrasound images. Based on the sub-sequence of the B-mode ultrasound images, a subsequence of the elasticity images is generated by selecting and/or modifying those elasticity images. Finally, the elastic modulus is determined based on the sub-sequence of the elasticity images. Also disclosed are a method for determining changes of the elastic modulus of a tissue, a method of identifying biological tissue based on the determined elastic modulus and a device for determining the elastic modulus of a biological tissue.

20 Claims, 3 Drawing Sheets

METHOD AND DEVICE FOR DETERMINING THE ELASTIC MODULUS OF A BIOLOGICAL TISSUE

Figure 1:
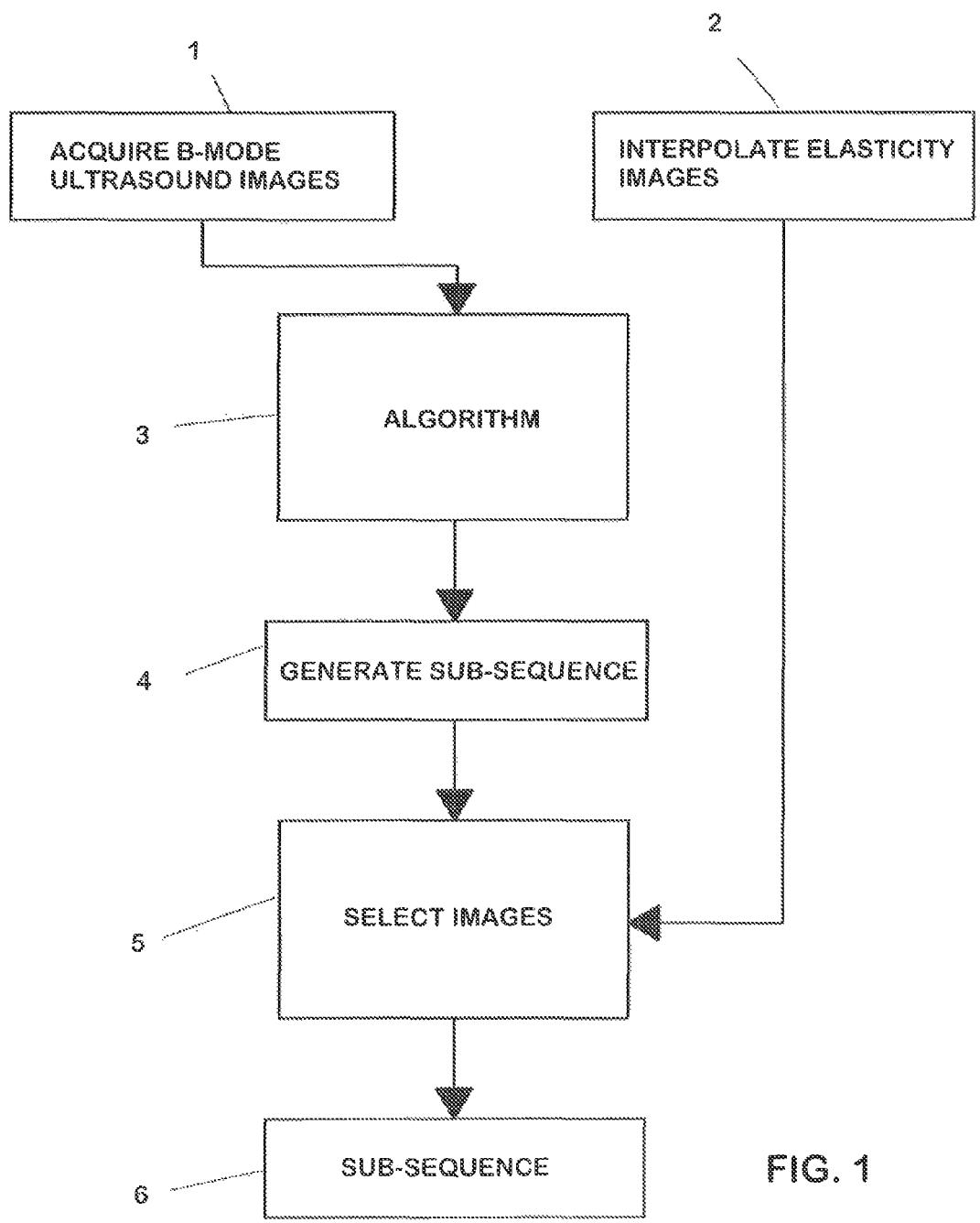

The present invention relates to a method for determining the elastic modulus, a method for determining changes of the elastic modulus, a method of identification of specific biological tissue based on the determination of the elastic modulus and a device for determining the elastic modulus of a region of interest in a body.

The determination of the elastic modulus of biological tissue by medical imagery serves various purposes both in the field of diagnosis and treatment. For example, as tissues exhibit differences in their elasticity, it is possible to differentiate cancerous tissue from benign tumours or healthy tissue by comparing their elastic modulus. Further, the efficacy of an ablative treatment, e.g. by means of laser or non-invasive high intensity focused ultrasound therapy may be monitored by determining changes of the elastic modulus of the tissue under treatment.

In the present application, the term "elastic modulus", is understood as a measure of the mechanical stiffness of an elastic material, such as biological tissue. When an external compression is applied to an elastic material, a deformation or strain is induced within said material. Harder material has a smaller induced strain than softer material.

Many tumours of the thyroid, breast, and prostate are still detected by manual palpation by a medical professional who senses abnormalities in the elasticity of the tissue. However, palpation is a subjective technique, and small abnormalities and those located in areas that are inaccessible by a physician cannot be detected by touch.

Hence, different imaging techniques were developed to be able to reliably determine the elastic modulus of biological tissues in a non-invasive, reliable and reproducible manner.

The so-called "static elastography" is relying on uniform compression of a portion of the body by a medical professional to cause a deformation in the underlying tissues. An ultrasound probe is then used to display the induced transformation in the imaging plane. However, static elastography shows poor reproducibility as well as variability depending on the specific medical professional applying the compression.

Another technique uses continuous vibration applied to a specific region of a body. The continuous vibration induces stationary waves within tissue which may be analyzed by means of magnetic resonance tomography. The elastic modulus of the tissue may be derived from the MRI imaging data.

A further technique is the so-called "shear wave elastography" which relies on the generation of shear waves within tissue. Shear waves propagate transversely in relation to the ultrasound beam within the tissue. The generated shear waves are detected by an ultra fast ultrasound system. As the waves travel at a speed between 1 and 10 m/s in human tissue, they cross a standard ultrasound imaging plane of 3 cm to 6 cm in 10-20 milliseconds (Bercoff Jeremy: The emergence of shear wave elastography in ultrasound; RAD Magazine; 36; 417; 32; February 2010). Hence, in order to capture the propagation of a shear wave, ultrasound imaging probes having frame rates of several thousands of images per second are needed. Such an ultrasound system is e.g. being sold under the name Aixplorer® by SuperSonic Imagine (Aix-en-Provence, France). The propagation of the shear waves in tissue induces small displacements, which may be detected and quantified using Doppler techniques. This allows generating a movie of the shear wave propagation within tissue. The shear wave propagation speed may then be estimated for each pixel of the acquired image from the shear wave propagation movie using appropriate algorithms. Young's modulus, defined as the ratio between the applied stress and the induced strain: $E=S/e$, are then calculated using the local shear wave propagation speeds. The elasticity modulus, displayed as elasticity images, correspond to the Young's modulus.

When acquiring elasticity images with an ultrasound probe, two channels may be obtained for each pixel, the first channel is representing the elasticity modulus of the tissue and the second channel is representing the pertinence of the measured value.

One mayor drawback of ultrasound elastography images is the low signal to noise ratio obtained. To increase this ratio, ultrasound devices often comprise a persistence function which allows applying a filtering algorithm on the last acquired images such as to improve the signal to noise ratio. Such persistence functions mostly rely on the determination of a weighted average, where the most recent images are weighted most, or a median value for each pixel based on a certain number of acquired images. The number of images used for the persistence function is usually selectable by the user of the ultrasound device. While persistence functions allow increasing the signal to nose ratio by averaging the acquired values of a certain number of images, any movement of the target area being measured will create a blurring effect on the image, as the position of the anatomy represented in the image is not constant anymore with respect to time, thus reducing the sharpness of the image.

It is therefore an objective of the present invention to provide a method for improving the quality of the elasticity image of a region of interest in a biologic tissue which avoids the disadvantages known in the art and in particular in case of movement of the tissue or the ultrasound probe head. This objective is achieved with a method as claimed in claim 1.

In a first step of the method according to the present invention, a sequence of elasticity images and a sequence of B-mode ultrasound images of a region of interest are acquired alternately. Then, at least one B-mode image sub-sequence representing a resting state of the region of interest is generated from said sequence of B-mode ultrasound images. In a third step, an elasticity image sub-sequence is generated by selecting and/or modifying those elasticity images based on said B-mode image sub-sequence. Finally, the elastic modulus of the region of interest is determined based on the elasticity image sub-sequence.

In the context of the present application, an "alternate" acquisition of a B-mode ultrasound image and an elasticity image has the meaning that a B-mode ultrasound image and an elasticity image are intermittently acquired. Hence, for every B-mode image $b(t)$ there is a corresponding elasticity image $e(t)$ which was acquired before the next B-mode image. This is preferably done by interpolation of both sets of images such as to allocate an elasticity image $e(t)$ to every B-mode ultrasound image $b(t)$ based on respective acquisition time-point. The interval between the acquisition of the B-mode image and the elasticity image is typically shorter than 1 ms. However, this will vary depending on the ultrasound probe used.

For a measurement having been acquired during the time period T, this allows the formation of two synchronized sets of images: one set being the B-mode ultrasound images $B=\{b(t)\}_{t \in T}$, the other set being the elasticity images $E=\{e(t)\}_{t \in T}$, wherein for each B-mode ultrasound image $b(t)$ there is a corresponding synchronized elasticity image $e(t)$.

The resolution of these digital images may vary depending on the device used. Hence, the number of pixels in the image will also vary. The acquired images may be 1, 2 or 3 dimensional images.

In the present application, the terminology "movement of the region of interest" is understood as either the region of interest is moved in relation to an ultrasound imaging probe, e.g. because of patient movements or breathing, or that the ultrasound imaging probe itself is moved, e.g. by changing its position in relation to the region of interest or by rotating or tilting the ultrasound probe. Hence, the term "resting state" has to be understood as meaning a temporarily invariant position of the region of interest in relation to the ultrasound probe head, e.g. because either the region of interest does not move or any movement is compensated by an algorithm.

From the sequence of acquired B-mode ultrasound images, a sub-sequence is generated. This B-mode image sub-sequence represents a resting state of the region of interest.

In a first alternative, the images selected for the B-mode image sub-sequence preferably show the region of interest without any movement or with only an insubstantial amount of movement.

Selection of appropriate images may be performed by an algorithm determining the positions of specific sections on an image and comparing these with the position of the same sections on another, preferably a reference image. If the positions are identical or almost identical, that a similarity value $\mu$ between the images is almost or exactly 1, the images are treated as showing the region of interest at a resting state. Statistical image analysis algorithms performing such tasks are well known in the art.

In a second alternative, the movement between images is compensated using a registration algorithm as known in the art, calculated on the set of B-mode images B. The spatial transformation used for each image is thereby stored. The registration algorithm optimizes the similarity value $\mu$ for each image in relation to another image, preferably a reference image.

The selection of an elasticity image sub-sequence is based on the B-mode image subsequence by selecting the appropriate synchronized elasticity images e(t) which correspond to the B-mode images b(t) of the B-mode image sub-sequence.

In an alternatively preferred embodiment, the generation of the elasticity image sub-sequence is performed by modifying each elasticity image with the same spatial transformation as the one which was determined for the image of the B-mode image sub-sequence acquired at the same time. By performing this operation, the images of the elasticity image sub-sequence are transformed in the same way as the B-mode images of the B-mode image sub-sequence, hence compensating any motion which occurred during their acquisition.

The images of both the B-mode image sub-sequence as well as the elasticity image sub-sequence are then fused, preferably pixel by pixel, to generate an enhanced B-mode image and an enhanced elasticity image. These reference images have an increased signal to noise ratio compared to any individual image.

There are different ways to fuse the images of both sub-sequences to generate the enhanced images. In one preferred method, the enhanced image is generated by calculating the median value for each pixel based on the corresponding pixel values of every image comprised in the respective image sub-sequence. For the enhanced elasticity image, the respective enhanced values for the elasticity channel and/or for the pertinence channel may be calculated.

In a further preferred method, the enhanced images are generated by calculating a weighted average for each pixel based on the respective pixel of every image in respective sub-sequence. The similarity value $\mu$ of each B-mode image is preferably used as weighting factor, since this allows images having a higher similarity to have a higher contribution to the enhanced image. When determining the enhanced elasticity image, the similarity value $\mu$ of the corresponding B-mode image is used.

Finally, the elastic modulus of the region of interest may be determined from the enhanced elasticity image in a known manner.

The method according to the present invention allows disregarding or correcting any movement of the region of interest based on the analysis of the B-mode ultrasound images, thanks to their higher signal to noise ratio and resolution compared to elasticity images. Therefore it is possible to greatly enhance the accuracy and the robustness of the elastic modulus determination from the elastography images.

In a first alternative, the B-mode image sub-sequence is generated by selecting B-mode ultrasound images from said acquired sequence of B-mode ultrasound images which have a similarity value $\mu$ with respect to a reference B-mode ultrasound image which is over a pre-selectable threshold value $s_\mu$. Different similarity measures are known in the art. For example the absolute value of the differences of the intensities is computed for each pixel and normalized. The similarity measure between the images is calculated as the normalized sum of the absolute value of the differences. This normalized value lies in the interval [0,1]. Such as to ensure a sufficient number of images in the B-mode image sub-sequence, a pre-selectable minimal number N of images may be defined. If the amount of selected images in the B-mode image sub-sequence is inferior to N, the sub-sequence is rejected since the number of images is statistically not sufficient to ensure the desired improvement of the signal to noise ratio for subsequently generated enhanced images.

Alternatively, a pre-definable number N of images which shall constitute the B-mode sub-sequence is selected. The acquired B-mode images are sorted according to their similarity value $\mu$ to a reference image in decreasing order. Of these images, the first N images are selected for the B-mode image sub-sequence. The average similarity value $\bar{\mu}$ of the images in the B-mode image sub-sequence is calculated and the B-mode image sub-sequence is only used if $\bar{\mu}$ is over a pre-selectable threshold value $s_\mu$. Otherwise, the sub-sequence is rejected since the average similarity of the images to the reference image is so low that an enhanced image generated therefrom would comprise too much blurring.

The elasticity image sub-sequence is generated by selecting those synchronized elasticity images which correspond to those B-mode ultrasound images selected for said B-mode image sub-sequence.

The threshold value $s_\mu$ may be chosen by the operator. The lower this threshold value is set, the more images are selected. However, these images will also exhibit less similarity to each other. The threshold value used by the user provides a trade off between increased signal to noise ratio (low threshold value) and sharpness (high threshold value) when computing the elastic modulus in a region of interest from the enhanced image as a final step.

The resting state reference image is preferably an image of the region of interest acquired before or during the acquisition of the image sequences.

In a second alternative, the B-mode image ultrasound sub-sequence is generated by applying a registration algorithm to the acquired images, preferably using a resting state reference image. The elasticity image sub-sequence is then generated by applying to each elasticity image the spatial transformation of the B-mode image corresponding to said elasticity image.

There are several registration algorithms known in the art which may be used to determine the appropriate spatial transformation, such as "gradient descent" or "simulated annealing".

By applying the spatial transformation of the corresponding B-mode ultrasound image to each elasticity image, the movement compensation determined on the B-mode ultrasound image may be applied to compensate the same movement of the region of interest on the elasticity image.

This method has the advantage that all the elasticity images of the sequence may be used to determine the elastic modulus of the region of interest, thus increasing the accuracy of the measurement compared to a method were several images of the sequence are not included in the sub-sequence because they were acquired when the region of interest was not in a resting state. Hence, this method allows generating a kind of "virtual resting state" of the region of interest, even though the region of interest moved during the acquisition of the sequence.

Preferably, a combination of the first and the second alternative methods described above may be applied to generate a B-mode ultrasound and an elasticity image sub-sequence. In this case, slight movements of the region of interest in B-mode ultrasound images selected for their sufficient similarity with the reference image may further be compensated. Such a combination further enhances the resulting determination of the elastic modulus of the region of interest.

Preferably, said resting state reference image is randomly selected from said acquired sequence of B-mode ultrasound images. Selection of a resting state reference image by this method is based on the assumption that no image is more relevant than any other.

Alternatively, said resting state reference image corresponds to the last B-mode ultrasound image acquired in said sequence.

Further preferably, said resting state reference image corresponds to a B-mode ultrasound image of the sequence which shows the highest similarity with a B-mode ultrasound image of the area of interest acquired prior to the acquisition of said elasticity image sequence and said sequence of B-mode ultrasound images.

Said resting state reference image is more preferably an enhanced B-mode image of an antecedent acquired sequence.

Hence, prior to generating the B-mode image sub-sequence, each B-mode ultrasound image of the sequence is compared by an appropriate algorithm to a resting state reference B-mode ultrasound image of the area of interest. For each B-mode ultrasound image of the sequence, the similarity value $\mu$ is determined and each B-mode ultrasound image of the sequence exhibiting a similarity value $\mu$ which is above a pre-selectable threshold is selected.

It is a further object of the present invention to provide a method for determining changes of the elasticity of a region of interest in biological tissue. This objective is achieved by a method as claimed in claim 8.

In this method according to the present invention, a differential elasticity image is generated by subtracting the acquired value of each pixel of a first enhanced elasticity image of a region of interest with the corresponding acquired value of each pixel of at least a second enhanced elasticity image of the same region of interest acquired at a different time point.

This allows to determine and to visualize the change(s) of the elastic modulus of biological tissue in a region of interest acquired at different time points. Such changes may e.g. be indicative of the evolution of tumour growth or the effects of an ablative therapy, such as treatment with High Intensity Focused Ultrasound (HIFU).

The enhanced elasticity images are preferably generated according to a method as described above.

Another object of the present invention is to provide a device for determining the elastic modulus of a region of interest in biological tissue. This objective is achieved with a device according to claim 10.

The device according to the present invention comprises an ultrasound probe adapted to acquire a sequence of elasticity images and a sequence of B-mode ultrasound images of the region of interest simultaneously. Further, the device includes means for generating at least one sub-sequence of the B-mode ultrasound images of the region of interest representing a resting state of the region of interest from said sub sequence of B-mode ultrasound images. Additionally, means for generating a sub-sequence of the elasticity images by selecting and/or modifying those elasticity images based on said sub-sequence of the B-mode ultrasound images are present in the device as well as means for determining the elastic modulus of the region of interest based on the sub-sequence of the elasticity images.

With a device according to the present invention it is possible to accurately determine the elastic modulus of biological tissue in a region of interest, even if the region of interest is moved during the acquisition of the elasticity images.

It is a further objective of the present invention to provide a method for identifying a specific biological tissue in a body. This objective is achieved with a method according to claim 11.

In a first step of the identification method according to the present invention the elastic modulus of a biological tissue is determined, preferably using a method for determining the elastic modulus of a region of interest in biologic tissue as described above. The biological tissue is then identified by comparing the determined elastic modulus with a database comprising reference values of the elastic modulus of different biological tissues. Finally, the thus identified biological tissue is displayed on an appropriate display.

This method offers the advantage that biological tissue can be easily and non-invasively identified based on its elastic modulus. Further, it is also possible to reliably and non-invasively detect cancerous tissue or tumours in a specific area.

A further objective of the present invention is to determine changes in elasticity of biological tissue in a region of interest. This objective is achieved by a method according to claim 13.

In a first step a first enhanced elasticity image of the region of interest is generated with a method as described above at a first time-point. At a second time-point, a second enhanced elasticity image of the region of interest is generated with a method as described above. Finally, a differential elasticity image is generated by subtracting the measured elasticity values of each pixel of the first enhanced elasticity image with the measured elasticity values of each corresponding pixel of the second enhanced elasticity image.

This method enables monitoring the effects of a heat treatment of tissue, such as treatment with High Intensity Focused Ultrasound (HIFU). As treated tissue will suffer heat damage, its elasticity will decrease. Hence it is possible to monitor the effect of the treatment by tracking changes of the elasticity in the region of interest.

Additionally, the enhanced B-mode images corresponding to both the first and the second enhanced elasticity images are compared and the similarity value μ is calculated. If this similarity value is below a pre-selectable threshold value $s_\mu$, the differential image is rejected. This enables to reject any differential image which was calculated using enhanced images which do not show the region of interest in a resting state or where the correction of movement is insufficient. That is, the generation of a differential image comprising too much blurring of the structures.

Further details and embodiments of the present invention will become apparent from the following description of figures and examples.

Figure 2:
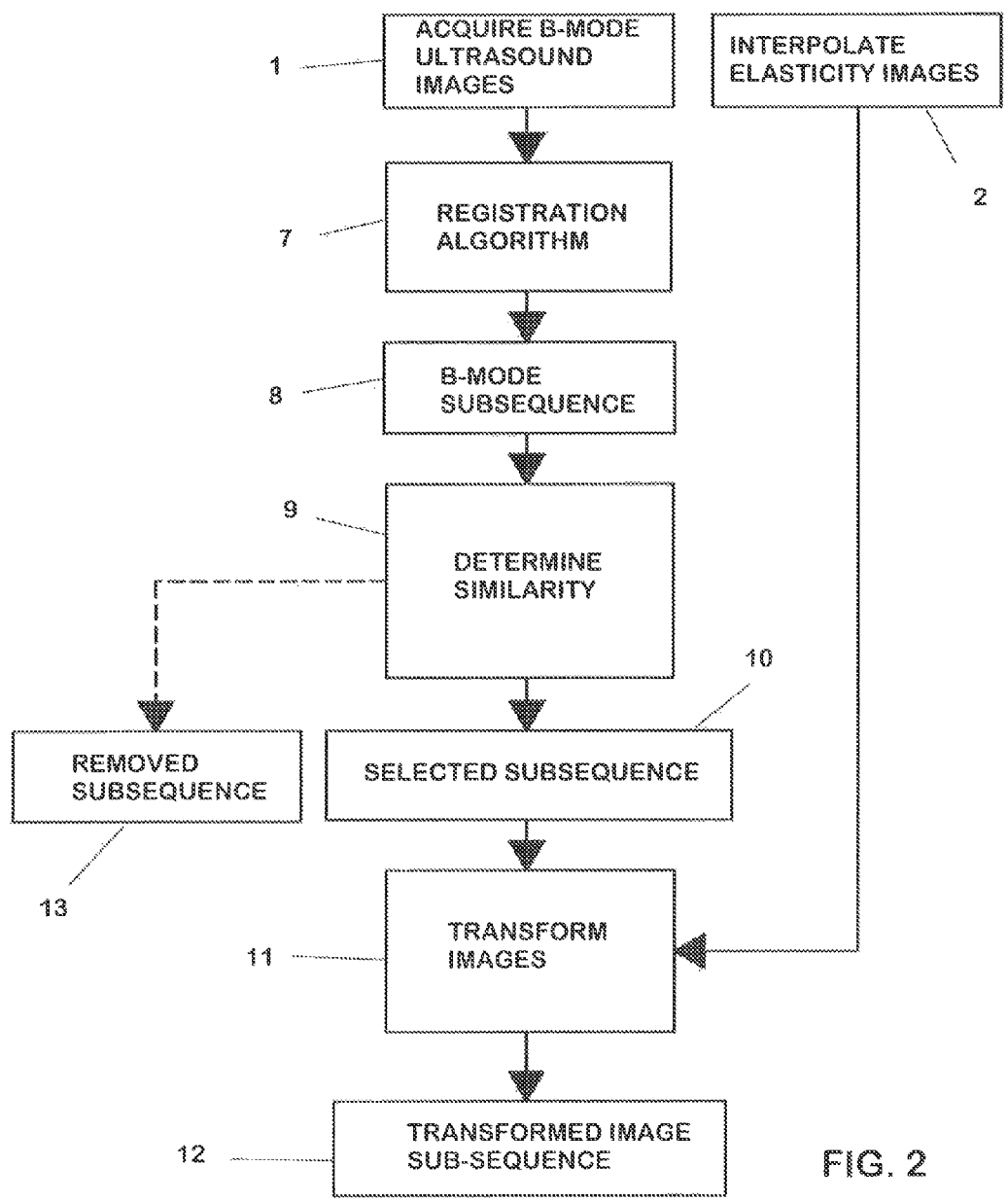
Figure 3:
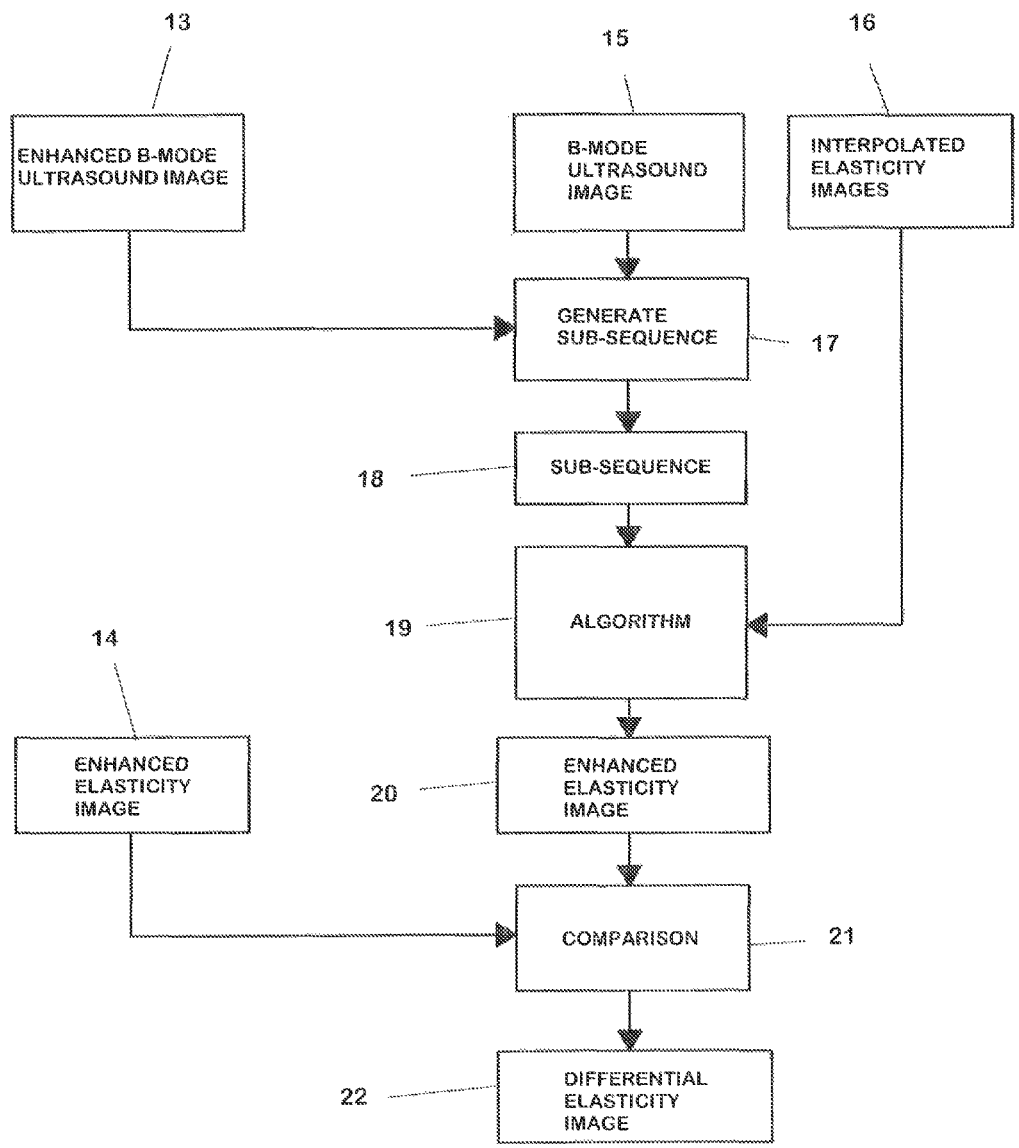

FIG. 1: Shows a schematic representation of a first embodiment of the present invention;

FIG. 2: shows a schematic representation of a second embodiment of the present invention; and FIG. 3: shows a schematic representation of a method to determine changes of elasticity of biological tissue in a region of interest.

FIG. 1 shows a schematic representation of a first embodiment of the method of determining the elastic modulus of an organic tissue in a region of interest according to the present invention. First, a sequence of B-mode ultrasound images 1 is acquired alternately with a series of elasticity images. By way of an interpolation of both sets of images, one elasticity image is allocated to every B-mode ultrasound image based on their respective acquisition time-point to generate a synchronized series of elasticity images 2. Then, a sub-sequence 4 of the B-mode ultrasound images 1 is generated by an appropriate algorithm 3, e.g. by determining the similarity μ of each B-mode ultrasound image to a reference B-mode ultrasound image. The reference B-mode ultrasound image is one particular image selected amongst the sequence of B-mode ultrasound images, preferably a randomly selected image or the last image acquired in the sequence. The images from the B-mode image sequence 1 which exhibit a similarity value μ to the reference B-mode image which is above a pre-defined threshold value $s_\mu$ are then selected to be included in the B-mode ultrasound image sub-sequence. This sub-sequence is stored in an appropriate memory device. In a further step 5, an algorithm selects those images from the synchronized elasticity image sequence 2, which correspond to those B-mode ultrasound images selected for the B-mode ultrasound sub-sequence 4. From this sub-sequence 6, an enhanced elasticity image is calculated by determining a median or averaged value for every pixel. The elastic modulus may then be derived from this enhanced image in a known manner.

FIG. 2 depicts a second embodiment of a method for determining the elastic modulus of biological tissue of a region of interest according to the present invention. In analogy to the embodiment shown in FIG. 1, a sequence of B-mode ultrasound images 1 is alternately acquired with a sequence of elasticity images and a synchronized sequence of elasticity images 2 is interpolated. A registration algorithm then determines and applies a spatial transformation to each image of the B-mode ultrasound image sequence in step 11, such that the similarity value μ of each B-mode ultrasound image is maximized in relation to a reference B-mode ultrasound image. The reference B-mode ultrasound image is one particular image selected amongst the sequence of B-mode ultrasound images, preferably a randomly selected image or the last image acquired in the sequence. The thus modified B-mode ultrasound images generate a B-mode ultrasound image sub-sequence 8. This B-mode sub-sequence 8 is preferably stored in an appropriate memory device, such as flash memory or the like. Further, the spatial transformation applied on each B-mode ultrasound image of the B-mode sub-sequence is also stored in an appropriate memory device. In step 9, an average similarity value $\bar{\mu}$ of the similarity values of all images of the B-mode image sub-sequence is determined. If this average similarity value $\bar{\mu}$ of the B-mode image sub-sequence is below a pre-defined threshold value $s_\mu$, the B-mode image 13 is removed from the B-mode ultrasound image sub-sequence 8. If the average similarity value $\bar{\mu}$ of the B-mode image sub-sequence 10 is higher than the threshold value $s_\mu$, the sub-sequence serves as a basis for generating an elasticity image sub-sequence 12 by an algorithm 11. The images of the synchronized elasticity image sequence 2 which correspond to the B-mode ultrasound images of the B-mode sub-sequence 11 are selected. Subsequently, the same spatial transformation operation is applied to these elasticity images as the spatial transformation which was applied to the corresponding B-mode ultrasound image. The thus generated elasticity image sub-sequence 12 comprises only elasticity images where any motion of the region of interest was compensated by the spatial transformation. From this sub-sequence 12, an enhanced elasticity image is calculated by determining a median or averaged value for every pixel. The elastic modulus may then be derived from this enhanced image in a known manner.

FIG. 3 shows a method to determine changes in the elasticity of an area of interest, e.g. to monitor the progress of a treatment, such as with High Intensity Focused Ultrasound. In analogy to the two methods described above, a sequence of B-mode ultrasound images 15 is alternately acquired with a sequence of elasticity images and a synchronized sequence of elasticity images 16 is interpolated. A B-mode image sub-sequence is generated from the sequence of B-mode ultrasound images using an enhanced B-mode ultrasound image 13 of the region of interest which was determined according to a method as described above at an earlier time-point, such as prior to the application of the treatment. By selecting images having a similarity value μ to the enhanced B-mode ultrasound image 13 used as reference image which is higher than a pre-selectable threshold value $s_\mu$ or by applying a registration algorithm using said enhanced image 13 as reference image, a B-mode image sub-sequence 18 is generated. From this B-mode image sub-sequence 18, an elasticity image sub-sequence 19 is extracted by an algorithm by selecting those synchronized elasticity images which correspond to the B-mode images of the B-mode image subsequence 18. From this sub-sequence, an enhanced elasticity image 20 is calculated, e.g. by averaging the measured values of each pixel in the sub-sequence. The elasticity values of each pixel of the enhanced elasticity image 20 are then compared to the elasticity values of each pixel of an enhanced elasticity image 14 which was determined at the same time as the enhanced B-mode image 13 used as reference image. The differences in elasticity are then shown in a differential elasticity image 22.

The invention claimed is:

1. Method for determining the elastic modulus of a region of interest in biologic tissue, to obtain stiffness information about the region of interest, comprising the steps of:
   acquiring a sequence of elasticity images and a sequence of B-mode ultrasound images of the region of interest alternately;
   generating at least one sub-sequence of the B-mode ultrasound images of the region of interest representing a resting state of the region of interest from said sequence of B-mode ultrasound images, to produce an image of the region of interest;

generating a sub-sequence of the elasticity images by at least one of (a) selecting only elasticity images corresponding to B-mode images representing the resting state of the region of interest and (b) modifying the elasticity images according to movement of the region of interest based on said sub-sequence of the B-mode ultrasound images; and determining the elastic modulus of the region of interest based on the sub-sequence of the elasticity images.

2. Method of claim 1, further comprising steps of identifying the biological tissue by comparing the determined elastic modulus with a database comprising values of the elastic modulus of different biological tissues; and displaying the thus identified biological tissue on a display for identifying a specific biological tissue in a body.

3. Method according to claim 1, wherein the sub-sequence of the B-mode ultrasound images is generated by selecting B-mode ultrasound images from said acquired sequence of B-mode ultrasound images having a similarity value μ to a reference B-mode ultrasound image superior to a pre-definable value and further wherein the elasticity image sub-sequence is generated by selecting those elasticity images which correspond to those B-mode ultrasound images selected for said B-mode ultrasound image sub-sequence.

4. Method according to claim 3, wherein said reference B-mode ultrasound image is randomly selected from said acquired sequence of B-mode ultrasound images.

5. Method according to claim 3, wherein said reference B-mode ultrasound image corresponds to a specific image acquired in said sequence.

6. Method according to claim 5, wherein said reference B-mode ultrasound image corresponds to the last B-mode ultrasound image of said sequence.

7. Method according to claim 3, wherein said reference B-mode ultrasound image corresponds to a B-mode ultrasound image of the sequence which shows the highest similarity with a B-mode ultrasound image of the area of interest acquired prior to the acquisition of said elasticity image sequence and said sequence of B-mode ultrasound images.

8. Method according to claim 1, wherein the sub-sequence of the B-mode ultrasound images is generated by determining and applying a spatial transformation to each B-mode ultrasound images of the sequence such as to maximize the similarity value μ of each B-mode ultrasound image to a reference B-mode ultrasound image of the region of interest, further wherein said elasticity images sub-sequence is generated by applying the same spatial transformation of the B-mode corresponding to each elasticity image.

9. Method according to claim 8, wherein said reference B-mode ultrasound image is randomly selected from said acquired sequence of B-mode ultrasound images.

10. Method according to claim 8, wherein said reference B-mode ultrasound image corresponds to a specific image acquired in said sequence.

11. Method according to claim 10, wherein said reference B-mode ultrasound image corresponds to the last B-mode ultrasound image of said sequence.

12. Method according to claim 8, wherein said reference B-mode ultrasound image corresponds to a B-mode ultrasound image of the sequence which shows the highest similarity with a B-mode ultrasound image of the area of interest acquired prior to the acquisition of said elasticity image sequence and said sequence of B-mode ultrasound images.

13. Method according to claim 1, wherein at least one of an enhanced B-mode ultrasound image and an enhanced elasticity image is generated by computing a median or average value for each pixel of the enhanced image from the corresponding pixels of at least one of all images of said B-mode ultrasound sub-sequence and from all images of said elasticity images sub-sequence.

14. Method for determining changes in elasticity of biological tissue in a region of interest, comprising the steps of:

generating a first enhanced elasticity image of the region of interest with the method according to claim 13 at a first time-point;

generating a second enhanced elasticity image of the region of interest with the method according to claim 13 at a second time-point; and generating a differential elasticity image by subtracting the measured elasticity values of each pixel of the first enhanced elasticity image with the measured elasticity values of each corresponding pixel of the second enhanced elasticity image.

15. Method for determining changes of the elasticity of a region of interest in biological tissue, wherein a differential elasticity image is generated by subtracting the acquired value of each pixel of a first enhanced elasticity image of a region of interest with the corresponding acquired value of each pixel of at least a second enhanced elasticity image of the same region of interest acquired at a different time point, wherein the enhanced elasticity images are generated according to the method of claim 13.

16. Method for determining changes of the elasticity of a region of interest in biological tissue, wherein a differential elasticity image is generated by subtracting the acquired value of each pixel of a first enhanced elasticity image of a region of interest with the corresponding acquired value of each pixel of at least a second enhanced elasticity image of the same region of interest acquired at a different time point.

17. Method according to claim 16, wherein a confidence level value is determined for each pixel of said differential elasticity image based on a similarity analysis of B-mode ultrasound images corresponding to first and the at least second elasticity images.

18. Device for determining the elastic modulus of a region of interest in biological tissue, comprising:

an ultrasound probe adapted to acquire a sequence of elasticity images and a sequence of B-mode ultrasound images of the region of interest alternately;

means for generating at least one sub-sequence of the B-mode ultrasound images of the region of interest representing a resting state of the region of interest from said sequence of B-mode ultrasound images;

means for generating a sub-sequence of the elasticity images by at least one of selecting and modifying those elasticity images based on said sub-sequence of the B-mode ultrasound images;

means for calculating enhanced images from at least one of said B-mode image sub sequence and said elasticity image sub-sequence; and means for determining the elastic modulus of the region of interest based on the enhanced elasticity image.

19. Device according to claim 18, wherein said device additionally comprises an ultrasound treatment probe head.

20. Device according to claim 19, wherein said device additionally comprises an ultrasound treatment probe head of the High Intensity Focused Ultrasound type.

* * * * *